United States Patent [19]

Schlossman

[11] Patent Number: 4,609,545

[45] Date of Patent: Sep. 2, 1986

[54] COMPRESSING AID FOR COMPRESSING POWDERS

[76] Inventor: Mitchell L. Schlossman, 20 Lakeshore Dr., Rockaway, N.J. 07886

[21] Appl. No.: 539,838

[22] Filed: Oct. 7, 1983

Related U.S. Application Data

[63] Continuation-in-part of Ser. No. 444,451, Nov. 24, 1982.

[51] Int. Cl.$^4$ .................. A61K 7/021; A61K 7/035; C08J 3/02
[52] U.S. Cl. .......................................... 424/63; 424/65; 424/69; 106/271; 514/844; 514/773
[58] Field of Search .............. 424/63, 64, 69, 65, 424/359; 106/271, 308 F; 514/773, 844

[56] References Cited

U.S. PATENT DOCUMENTS

| | | | |
|---|---|---|---|
| 684,522 | 10/1901 | Painter | 106/151 |
| 1,396,837 | 11/1921 | Hartong | 524/21 |
| 1,707,684 | 4/1929 | Picker | 424/69 X |
| 1,996,168 | 4/1935 | Ornfeldt | 424/69 |
| 2,320,098 | 5/1943 | Quisling | 424/63 |
| 2,436,818 | 3/1948 | Musher | 424/49 |
| 2,536,339 | 1/1951 | Wood et al. | 106/37 |
| 2,657,148 | 10/1953 | Ehrlich | 106/153 |
| 2,711,378 | 6/1955 | Holtzinger | 427/394 |
| 3,300,387 | 1/1967 | Kole | 424/66 X |
| 3,800,034 | 3/1974 | Kircher et al. | 424/63 |
| 3,847,622 | 11/1974 | Brandl et al. | 106/271 X |
| 3,911,105 | 10/1975 | Papantoniou et al. | 424/63 |
| 4,049,792 | 9/1977 | Elsnau | 424/66 |
| 4,279,890 | 7/1981 | Harris et al. | 424/69 |
| 4,305,931 | 12/1981 | Kawano et al. | 424/69 |
| 4,379,136 | 5/1983 | Mochida | 424/65 |
| 4,404,035 | 9/1983 | Ona et al. | 106/271 |

FOREIGN PATENT DOCUMENTS

| | | | |
|---|---|---|---|
| 0136213 | 10/1980 | Japan | 424/63 |
| 7112315 | 7/1982 | Japan | 424/68 |

OTHER PUBLICATIONS

The Encyclopedia of Polymer Science and Technology, vol. 14, pp. 768–779.

Primary Examiner—Esther M. Kepplinger
Assistant Examiner—Shawn P. Foley
Attorney, Agent, or Firm—Handal & Morofsky

[57] ABSTRACT

The compressing aid consists of particles of a Fischer-Tropsch synthetic saturated hydrocarbon wax having an average molecular formula of $C_{48}H_{98}$, an average molecular mass of about 700, a minimum congealing point of about 204° F. and an average particle size of about 10 microns. For greater ease and dispersion during blending of the ingredients, the wax particles may be coated with 0.1 to 1.0% by weight of a lubricant such as dimethyl polysiloxane, isopropyl myristate, lauryl lactate or ethylhexyl palmitate. As an alternative to using these lubricants, coating the surface of the wax with about 0.10–0.20% of a protein zein of corn gluten lubricates the fine wax and aids in its dispersion in the particle mixture. In many applications the vegetable protein lubricant is preferably because less pressure is needed to compress the mixture than with the lubricants noted above.

5 Claims, No Drawings

COMPRESSING AID FOR COMPRESSING POWDERS

CROSS REFERENCE

This application is a continuation in part of U.S. application Ser. No. 444,451 of Schlossman, filed on Nov. 24, 1982 for COMPRESSING AID FOR COSMETIC POWDERS, the disclosure of which is incorporated herein by reference.

TECHNICAL FIELD

The present invention relates to cosmetic compositions and particularly relates to a compressing aid for cosmetic powders, such as face powder, blusher, eye shadow, or the like and is also useful in the manufacture of anti-perspirant sticks.

BACKGROUND ART

Cosmetic powders are currently available in loose and pressed form. The majority of these powders, face powder, blusher, eye shadow, etc., are used in pressed form. This form of the product is very practical since it is easy to carry along and can be used whenever needed for touching up. The desirable properties of a pressed powder are: easy powder release without dustiness, good skin adhesion, and a strong cake which does not crumble, break, or cake up. In order to achieve all of these characteristics, the present pressed powder formulations contain a blend of several ingredients, each chosen for their specific quality.

The major constituents of a regular shaded pressed powder are talc and color; all other ingredients being used to achieve compressibility. Binding is a special property inherent to pressed powder formulation. Most powder constituents found in formulations are not "binding" in themselves and therefore other agents such as metallic stearates, kaolin, and fatty materials are used as additives to insure proper adhesion and compressibility. Fatty materials, such as mineral oil or fatty alcohols, are used in liquid form to aid in binding, improve adhesion to the skin, and reduce cake dustiness.

In frosted products, mica and titanium dioxide coated mica (pearlescent materials) are the major powder constituents. In order to compress these materials, a large portion of about 20 to 40 percent of a composition is added. Such large amounts of non-pearlescent ingredients reduced the "frosty" effect of the product.

With current methods, manufacturing of a pressed powder is long and tedious. It involves blending of all dry powder ingredients, wetting the blend with the liquid fatty material and can lead to subsequent balling up of the powder. In order to break up the powder balls and achieve a uniform liquid distribution within the powder, it must then go through a micropulverization process. The inability to hold a shape after compression may vary with the chemical origin of the binding agent and the percentage utilized in the pressed powder formulation. A great many such formulations are possible. See for example, De Navarre, *The Chemistry and Manufacture of Cosmetics*, Vol. 4 Continental Press, Fla. 1974.

In the past many methods of aggregating inherently non-cohesive powders were used. For example, Ornfeldt, in U.S. Pat. No. 1,996,168 discloses a jelly-like substance which might be used. 1-5% of beeswax or synthetic wax and a small amount of soap are combined in melted form with mineral oil and heated. After cooling the mixture, powdery materials such as talc are added. The jelly-like substance will increase the surface cohesiveness of the powder and keep it from dusting. No mention is made of compressing this powdery product, nor is it likely that this would constitute a suitable method for aggregating a powder which is to remain substantially dry, such as face powder.

Picker, in U.S. Pat. No. 1,707,684 employs olive oil as a waterproof binder for powder in loose form. Olive oil might be used as a cosmetic additive for its emolient properties, however, it does have a tendency to turn rancid. Moreover, it is doubtful that olive oil would provide sufficient cohesiveness to form a strong cake of powder.

Kole in U.S. Pat. No. 3,300,387 discloses a pressed powder consisting of an anti-perspirant coated with 5-15% of a water soluble wax-like material such as PEG and its methoxy derivatives mixed with a powder base and an oily binder such as mineral oil, lanolin, vegetable oils and isopropyl esters of fatty acids. The pressed powders of U.S. Pat. No. 3,800,034 to Kircher et al. contain binders such as gum, cellulose derivatives, gelatin, lignin, PVP, PVA and a complex magnesium silicate and lubricants such as metal stearates, liquid paraffin, fatty alcohols, fatty acids and oils. Harris et al., in U.S. Pat. No. 4,279,890 use metal stearates as binder and lubricant in pressed powders. Prevention of cracking in pressed powders was provided in U.S. Pat. No. 4,305,931 to Kawano et al. by incorporating a hydroxypropyl-etherified glycolipid ester.

Despite the advances noted above, manufacturing of a pressed powder with conventional ingredients is a long involved multi-step process wherein the ingredients are handled repeatedly in order to achieve the desired properties. This explains, in part the high cost of certain cosmetics and their failure to meet performance criteria. Anti-perspirant sticks can be produced by combining active particulate ingredients such as aluminum chlorohydrate with a low melting point wax and melting the mixture so that an anti-perspirant stick can be formed from the hot wax. This is an expensive process in terms of energy consumption and results in a wet, greasy, wax-like product which is unpleasing to the touch. This process is frequently used to produce anti-perspirant sticks because a suitable compressing aid which would allow the dry manufacture of many such products is unavailable.

SUMMARY OF THE INVENTION

The present invention relates to pressed compositions for personal use and particularly relates to a compressing aid for such products.

It is accordingly the object of the present invention to eliminate the addition of a large concentration of additives to pressed powders.

It is another object of this invention to increase the pearlescent effect of the product by reducing the concentration of additives.

It is another object of this invention to eliminate the addition of a liquid binding agent. This eliminates the need for adjusting wetting agents for oil absorption of pigment concentration.

It is a further object of this invention to drastically reduce processing time required of pressed powders; effecting cost savings.

It is another object of the present invention to provide pressed powders which have good compressibility, low dusting, sufficient powder release without glazing, good adhesion, smooth surface, and a strong cake without crumbling, therefore improving shipping qualities.

In accordance with the present invention it has been found that when a synthetically prepared saturated hydrocarbon wax, either alone or treated with a lubricant such as a low viscosity fatty ester or silicone fluid, or a water insoluble prolamine (protein) of corn gluten, can act as a compressing aid for pressed powders to obtain the above mentioned objects.

BEST MODE FOR CARRYING OUT THE INVENTION

The synthetically prepared saturated hydrocarbon wax is in powdered form with an average particle size of about ten microns. As stated the wax itself can act as a compressing aid, but is difficult to disperse uniformly in small concentrations within the powder because of its tackiness. Coating the surface of the wax particles with about 0.1 to 1 percent of a fatty ester or a silicone fluid lubricates the fine wax and aids in its dispersion. The synthetically prepared saturated hydrocarbon wax, obtained by the Fisher-Tropsch catalytic hydrogenation of carbon monoxide at high temperature and pressure, is in powder form and obtained from a number of suppliers. The saturated hydrocarbon wax has a formula $C_nH_{2n+2}$ with an average molecular formula of $C_{48}H_{98}$ and an average molecular mass of 700. It is a hard, brittle, high melting wax powder, with a congealing point of about 204° F. minimum. The firm of Mooret Munger Marketing Inc. supplies the wax under the trade name Paraflint ® H1; however the wax is available under other trade names such as Efto Fine Wax Powder, or Microfine Hard Wax.

The small particles of wax when properly dispersed will impart compressibility to non-compressing systems even when present in a concentration of 10 percent or less by weight. For example, such a system made up of talc and the wax will exhibit the desirable qualities of a pressed cosmetic powder noted above if mechanically compressed with a force in the range of 1500 PSI.

As noted earlier, it is difficult to disperse the wax uniformly in a powder system because of its tackiness. Accordingly, it is sometimes desirable to coat the wax particles with low viscosity esters of fatty acids or alcohols having 10-18, preferably 12-16, carbon atoms. Examples of such esters are isopropyl myristate, laury acetate, and ethylhexyl palmitate.

Alternatively, the wax particles could be coated with a silicone fluid, such as dimethyl polysiloxane, a water immiscible silicon oil consisting of dimethyl siloxane polymer. The CTFA name is Dimethicone.

Treatment of the wax particles with the ester or silicone is carried out in a high speed blender, such as a "Munson Rotary Batch Mixer" or a "Baker-Perkins Dry Dispenser", by spraying the liquid into the powder in the blender.

The above coating on the wax is not needed if the wax is predispersed in a base, such as mica, talc, etc. It should be noted that neither the ester or silicone materially effects the properties of the pressed powder when completed; however, dispersion is greatly aided.

| Ingredients | w/w % |
|---|---|
| Example I | |
| Pearly Material *(colored) | 90.00 |
| Compressing Aid (uncoated wax) | 10.00 |
| | 100.00 |

| Ingredients | w/w % |
|---|---|
| Example II | |
| Talc | 90.00 |
| Iron Oxide Pigments | 4.00 |
| D & C Organic Lakes | 1.00 |
| Compressing Aid (ester coated wax) | 5.00 |
| | 100.00 |
| Example III | |
| Mica Classified Particle Size | 85.00 |
| Iron Oxide Pigments | 5.00 |
| Compressing Aid (silicone coated wax) | 10.00 |
| | 100.00 |

*Presperse Colors sold by Presperse Inc., South Plainfield, New Jersey.

The manufacturing of the pressed powders according to the invention is very simple and involves blending the compressing aid with the pigments, mica talc, etc., and compressing the mixture into godets. Micropulverization is only needed if the pigment particle size needs to be reduced.

A comparison was made of pressed powders according to the invention with two similar pressed powders currently on the market. The following table shows the advantages of the invention, especially in the frost composition. The tests were run with two products of the cream shade type and two of the frost type in accordance with the invention. One of each type incorporated the uncoated synthetic wax as compressing aid and the other of each type incorporated the coated wax as compressing aid. Although the coated wax blended more easily with the other ingredients, the properties of the final product were the same. The cream shade base consisted of talc and iron oxide and the frost base consisted of titanium dioxide and mica.

| | Pressed Powders | |
|---|---|---|
| Properties | Cream Shade | Frost |
| | Currently on the Market | |
| Compressibility | good | poor |
| Powder Release | good | too much |
| Glaze | yes | no |
| Dustiness | no | yes |
| Skin Adhesion | good | poor |
| Wear | good | fair |
| Crumbling | no | yes |
| | Made with Compressing Aid | |
| Compressibility | good | good |
| Powder Release | good | good |
| Glaze | no | no |
| Dustiness | no | no |
| Skin Adhesion | good | good |
| Wear | good | good |
| Crumbling | no | no |

As another way of aiding dispersion of the wax described above into other products, coating the surface of the wax particles with about 0.1-0.20% of a vegetable protein. In particular, a protein of corn gluten known as zein was found to be particularly adventageous for lubricating the fine wax particles and aiding in their dispersion. The corn gluten increased the compressibility of the system. Less than 0.10 weight percent is insufficient for good dispersion and increased compressibility and excessive protein can cause brittleness. Generally, more than about 0.2% by weight is undesirable. It might by noted that several hydrolyzed animal proteins were found unevitable.

The corn gluten protein used to coat the wax has an approximate molecular weight of 35,000 and an approximate specific gravity of 1.25 at 25° C. and is 88–96 percent active protein (zein), calculated on a dry basis. Suitable grades of zein are available from Freeman Industries, Inc. of Tuckahoe, N.Y. The product marketed by Freeman Industries is generally smaller than 20 mesh. It should be noted that zein is insoluble in water.

The treatment of the wax particles with the protein is carrierd out in a high speed blender, such as a Paterson-Kelley Twin Shell Blender with intensifier bar, jacketed for heating and having vacuum capability. Such a device is available from the Paterson-Kelley Company of East Stroudsburg, Pa. The powdered wax is treated with the protein in the following manner:

15 kg of synthetic saturated Fischer-Tropsch hydrocarbon wax as described above is charged into the blender and mixed 4 or 5 minutes with the intensifier bar to break up lumps. 308 gms of a coating solution comprising 20% deionized water, 75% isopropyl alcohol, and 5% (2–4% aqueous) corn gluten protein solution are metered through the intensifier bar at 200 gms per minute. The mixture is blended with the intensifier bar for one minute after liquid addition. The heating medium, water at 100° F., is then circulated through the jacket of the blender. A vacuum of 6 mm Hg is applied in order to dry the mixture. The required drying time is about 10 minutes. Solvent is recovered via a condenser in the vacuum line.

The following are examples of typical formulations using the compressing aid comprising the wax coated with protein as described.

| Ingredients | w/w % |
|---|---|
| Example IV | |
| Talc | 90.00 |
| Iron Oxides (pigments) | 5.00 |
| Compressing Aid (wax coated w/protein) | 5.00 |
| | 100.00 |
| Example V | |
| Mica Classified Particle Size | 85.00 |
| Iron Oxide Pigments | 5.00 |
| Compressing Aid (wax coated w/protein) | 10.00 |
| | 100.00 |

In the above examples, the iron oxide pigments and the D&C organic lakes are conventional cosmetic coloring materials, such as those sold by Clark Colors Inc. Talc and mica are also conventional powder components of pressed powders and are used in the particle size normally suitable for such products. Talc is more easily compressed than mica, as is known, and this accounts for the larger amounts of compressing aid required in Examples I and III employing mica as compared to Example II employing talc.

The manufacturing of the pressed powders according to the invention is quite simple and involves blending the compressing aid with the pigments, mica, talc etc., and compressing the mixture into godets or stick form. This can be done using any suitable means, such as an Arenco Alite Compressed Powder Machine. Micropulverization is needed if the pigment particle size needs to be reduced.

A comparison was made of pressed powders produced with the protein coated wax with similar pressed powders made with synthetic saturated hydrocarbon wax alone and powders made with synthetic saturated hydrocarbon wax coated with silicone as noted previously.

It was found that the product made with the compressing aid with protein required less pressure in order to form a product with the desired properties. For example 1,000 PSI was sufficient to compress the mixture with the protein coated compressing aid, however, 1,500 PSI was required to produce a cake with the same hardness using the compressing aid alone or the wax coated with silicone. When compared in a drop test, the protein coated product produced a firmer, more stable cake. The drop test consists of placing the pressed powder in a pan and dropping the pan from a height of approximately 2 feet on to a hard rubber mat three times. If the powder does not fracture it is deemed to have passed the test.

All of the examples noted above had very similar attributes as relating to the elimination of the addition of a large concentration of additives in order to increase the pearlescent effects of pressed powders, and eliminating the need for addition of a liquid binding agent. Processing time for pressed powders is substantially reduced. All examples noted above have significant improvements over conventional pressed powders or pressed powder processing techniques. The protein coated wax, in particular, had improved compressibility, low dusting, sufficient powder release without glazing, excellent skin adhesion, a smooth surface, and improved shipping qualities by providing a stronger cake.

The wax coated with protein described above in also useful for use is an anti-persperant stick having the general formulation indicated below:

| Antiperspirant Stick | w/w % |
|---|---|
| Aluminum Chlorohydrate (Impalplable Powder, 300 mesh) | 15–25 |
| Talc (325 Mesh) | 65–75 |
| Compressing Aid (wax coated w/protein) | 8–12 |
| | 100.00 |

An anti-perspirant stick having the general formulation shown in Example VI is produced in substantially the same manner as the pressed powders described earlier, by simply pressing the powders. An inexpensive method of producing a very dry anti-perspirant stick with existing equipment is thus provided.

Naturally, some modification of the disclosed embodiment will be obvious to those of ordinary skill in the art. For example, the aluminum chlorohydrate of Example VI may be replaced by an aluminum zirconium complex.

I claim:

1. In a compressed product for personal use comprising powdery ingredients, the improvement which comprises the combination of said powdery ingredients with an effective amount of compressing aid consisting of particles of a Fischer-Tropsch, synthetic saturated hydrocarbon wax having an average molecular formula of $C_{48}H_{98}$, an average molecular mass of about 700, a minimum congealing point of about 204° F., and an average particle size of about 10 microns, said wax being coated with from about 0.1 to 2.0% by weight, based on the weight of the wax, of a lubricant which comprises at least one vegetable protein.

2. The pressed product of claim 1, wherein said vegetable protein is zein.

3. The pressed product of claim 1 wherein said compressing aid is used in the compressed product in the amount of about 5 to 15% by weight.

4. The pressed product according to claim 2 wherein said powdery ingredients comprise at least one component selected from the group consisting of talc, mica and titanium dioxide coated mica and at least one component selected from the group consisting of iron oxide pigments and organic lakes.

5. The pressed product according to claim 2, wherein said powdery ingredients comprise aluminum chlorohydrate and talc.

* * * * *